(12) United States Patent
Kim et al.

(10) Patent No.: US 9,458,448 B2
(45) Date of Patent: Oct. 4, 2016

(54) MANUFACTURING METHOD FOR SILICA ENCAPSULATED SINGLE-ENZYME NANOPARTICLES AND SINGLE-ENZYME NANOPARTICLES MANUFACTURED BY MEANS OF METHOD

(75) Inventors: Jungbae Kim, Seoul (KR); Sung-Gil Hong, Seoul (KR); Byoungsoo Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 26 days.

(21) Appl. No.: 14/112,834

(22) PCT Filed: May 23, 2012

(86) PCT No.: PCT/KR2012/004053
§ 371 (c)(1),
(2), (4) Date: Jan. 17, 2014

(87) PCT Pub. No.: WO2012/161502
PCT Pub. Date: Nov. 29, 2012

(65) Prior Publication Data
US 2014/0127778 A1  May 8, 2014

(30) Foreign Application Priority Data
May 23, 2011 (KR) .................. 10-2011-0048437

(51) Int. Cl.
| | |
|---|---|
| C12N 9/96 | (2006.01) |
| C12N 11/14 | (2006.01) |
| G01N 33/543 | (2006.01) |
| C12N 9/20 | (2006.01) |
| B01J 13/14 | (2006.01) |
| B82Y 40/00 | (2011.01) |

(52) U.S. Cl.
CPC .................. *C12N 9/96* (2013.01); *B01J 13/14* (2013.01); *C12N 9/20* (2013.01); *C12N 11/14* (2013.01); *G01N 33/54346* (2013.01); *B82Y 40/00* (2013.01)

(58) Field of Classification Search
None
See application file for complete search history.

(56) References Cited

U.S. PATENT DOCUMENTS

2012/0283379 A1* 11/2012 Auger et al. .................. 524/556

FOREIGN PATENT DOCUMENTS

WO  WO 2011058046 A1 *  5/2011

OTHER PUBLICATIONS

Popat, A. et al."Mesoporous silica nanoparticles for bioadsorption, enzyme immobilisation, and delivery carriers", Nanoscale 2011 (published online on May 5, 2011), vol. 3, pp. 2801-2818.*
International Search Report for Application No. PCT/KR2012/004053 dated Dec. 26, 2012.
Cao, A. et al., *A Facile Method to Encapsulate Proteins in Silica Nanoparticles: Encapsulated Green Fluorescent Protein as a Robust Fluorescence Probe,* Angew. Chem. Mar. 22, 2010, vol. 122, pp. 3086-3089.
Hegedus, I. et al., *Improvement of Chymotrypsin Enzyme Stablility as Single Enzyme Nanoparticles,* Chemical Engineering Science, Nov. 17, 2008, vol. 64, pp. 1053-1060.
Hong, R. et al., *Monolayer-controlled Substance Selectively Using Noncovalent Enzyme-Nanoparticle Conjugates,* J. Am. Chem. Soc., Sep. 29, 2004, vol. 126, pp. 13572-13573.
Kim, Jr. et al., *Single Enzyme Nanoparticles in Nanoporous Silica: A Hierarchical Approach to Enzyme Stabilization and Immobilization,* Enzyme and Microbial Technology, Jul. 3, 2006, vol. 39, pp. 474-480.
Domach, M. and Walker, L. "Stabilizing biomacromolecules in nontoxic nano-structured materials." Journal of Association for Laboratory Automation, Apr. 2010, vol. 15. pp. 136-144.
Gupta et al., "Silica Nanoparticles Coencapsulating Gadolinium Oxide and Horseradish Peroxidase for Imaging and Therapeutic Applications." International Journal of Nanomedicine, 2012:7, 2012, pp. 5491-5500.
Jain et al. "Nanometer Silica Particles Encapsulating Active Compounds: A Novel Ceramic Drug Carrier." Journal of the American Chemical Society, vol. 120, No. 43, 1998, pp. 11092-11095.
Yang et al. "Magnetite-Containing Spherical Silica Nanoparticles for Biocatalysis and Bioseparations." Analytical Chemistry, vol. 76, No. 5, Mar. 1, 2004, pp. 1316-1321.
English Translation of Written Opinion for Application No. PCT/KR2012/004053 dated Dec. 26, 2012, 5 pages.

* cited by examiner

Primary Examiner — Renee Claytor
Assistant Examiner — Michelle F Paguio Frising
(74) Attorney, Agent, or Firm — Alston & Bird LLP (57) ABSTRACT

A method for manufacturing single enzyme nanoparticles through silica encapsulation according to the present disclosure does not include a surface functionalization process and a polymerization process during the synthesis, and reaction conditions are mild. Thus, the method is appropriate for a large scale production.

4 Claims, 5 Drawing Sheets

MANUFACTURING METHOD FOR SILICA ENCAPSULATED SINGLE-ENZYME NANOPARTICLES AND SINGLE-ENZYME NANOPARTICLES MANUFACTURED BY MEANS OF METHOD

CROSS-REFERENCE TO RELATED APPLICATIONS

This application is a national stage application filed under 35 U.S.C. 371 of International Application No. PCT/KR2012/004053, filed May 23, 2012, which claims priority to Korean Patent Application No. 10-2011-0048437, filed on May 23, 2011.

TECHNICAL FIELD

The present disclosure relates to single enzyme nanoparticles and a method for manufacturing the same through silica encapsulation, more particularly to a method for manufacturing silica encapsulated single-enzyme nanoparticles in a large scale by a much simpler process than the existing method and single enzyme nanoparticles prepared thereby.

BACKGROUND ART

Traditionally, the sol-gel method has been used to synthesize organic-inorganic composites including enzymes to improve the stability of the enzymes in organic or aqueous solutions. In most applications, silica-encapsulated enzymes are synthesized in two stages by the sol-gel method. In the first stage, silica monomers are hydrolyzed in an aqueous solution containing enzymes. In the second stage, the hydrolyzed silica monomers encapsulate the enzymes as they are condensed, thus forming a growing silica network. Through this procedure, a sol-gel matrix in which silica is hydrolyzed and condensed is formed. However, the sol-gel matrix approach for encapsulating enzymes induces mass transfer limitation against substrates diffusion through the thick sol-gel matrix.

Enzyme encapsulation is frequently used as one of the enzyme immobilization methods for caging and stabilization of the enzymes. However, according to most researches, sol-gel composites in a few micrometers to millimeters range restricted the transfer of substrate molecules from medium to active sites of enzymes. Accordingly, the sol-gel encapsulation method could stabilize the individual enzyme molecules while increasing a Michaelis-Menten constant, so draws a lot of attentions. Another general approach is to form reverse micelles. However, the reverse micelles are including large quantity of water molecules, which can form sol-gel matrix via silica hydrolysis and condensation. Consequently, the thick sol-gel matrix causes serious mass transfer limitation against substrates diffusion from medium to active site of enzyme.

Currently, it is reported that single enzyme nanoparticles (SENs) are obtained by forming an organic-inorganic hybrid polymer network of less than a few nanometers thick without entirely encapsulating the enzyme aggregates. Specifically, the synthesis of the SENs begins with solubilization of enzyme molecules in a hexane solution. The solubilization process, which uses smaller amount of surfactant than the reverse micelle approach, involves extracting individual enzyme molecules with the organic solvent while preventing aggregation of the enzymes. The surface of the solubilized enzymes is exposed to the organic solvent together with the minimal amount of water molecules. This is very important for successfully forming SENs with a very thin network. However, the synthesis of the SENs necessarily requires formation of the functional groups on the surface of the enzymes in hexane and polymerizing them by using the functional groups, for example, vinyl groups. Since the radical polymerization process is very complicated and sensitive to reaction condition, it is very difficult to produce SENs in a large scale.

DISCLOSURE

Technical Problem

The present disclosure is directed to a method for manufacturing single enzyme nanoparticles via silica hydrolysis and condensation, which allows a large scale production by forming single enzyme nanoparticles with thin silica network, without functionalization on the surface of the enzyme and a radical polymerization process, and provides a Michaelis-Menten constant ($K_m$) comparable to that of free enzymes.

The present disclosure is also directed to silica encapsulated single-enzyme nanoparticles wherein an extremely thin silica network is formed on the surface of the enzymes without forming additional functional groups or attaching polymers thereon and the margin of error of the Michaelis-Menten constant ($K_m$) is very small as compared to free enzymes.

Technical Solution

In one general aspect, the present disclosure provides a method for manufacturing silica encapsulated single-enzyme nanoparticles, including: (1) solubilizing enzymes from an aqueous solution to an organic solvent; (2) adding silica monomers to the organic solvent and hydrolyzing the silica by reacting with water molecules on the surface of the solubilized enzymes; (3) back-extracting the enzymes from the organic solvent into an aqueous solution; and (4) condensing the silica in an aqueous solution.

In an exemplary embodiment of the present disclosure, the aqueous solution may be one or more selected from a group consisting of a Bis-Tris propane aqueous solution, a sodium phosphate aqueous solution, a Tris aqueous solution and a sodium bicarbonate aqueous solution and the organic solvent may be a hydrophobic organic solvent.

In another exemplary embodiment of the present disclosure, a step (1) may be performed by adding a solubilizing agent.

In another exemplary embodiment of the present disclosure, the solubilizing agent may be a surfactant at or below the critical micelle concentration.

In another exemplary embodiment of the present disclosure, the silica in a step (2) may be one or more selected from a group consisting of tetramethoxysilane, trimethoxysilane, dimethoxysilane, tetraethoxysilane, triethoxysilane and diethoxysilane.

In another exemplary embodiment of the present disclosure, a step (3) may be performed by adding a back extraction solution.

In another exemplary embodiment of the present disclosure, the back extraction solution may be one or more selected from a group consisting of a Bis-Tris propane aqueous solution, a sodium phosphate aqueous solution, a Tris aqueous solution and a sodium bicarbonate aqueous solution.

In another exemplary embodiment of the present disclosure, the method may further include separating an aqueous solution layer by stirring and centrifugation between step (3) and step (4).

In another exemplary embodiment of the present disclosure, step (4) may be performed at 1-40° C.

In another general aspect, the present disclosure provides silica encapsulated single-enzyme nanoparticles comprising enzyme nanoparticles and a silica network surrounding the enzyme nanoparticles individually, wherein have pores, and wherein no covalent bond is formed between the enzyme surface and the silica network.

In another exemplary embodiment of the present disclosure, the silica encapsulated single-enzyme nanoparticles may have a Michaelis-Menten constant ($K_m$) value with a margin of error not greater than 20%, more specifically not greater than 10%, further more specifically not greater than 5%, most specifically not greater than 3%, as compared to that of free enzymes.

In another exemplary embodiment of the present disclosure, the silica capsule may have a thickness of 0.5-2.5 nm.

In another exemplary embodiment of the present disclosure, the silica capsule may not include vinyl polymers on the surface of the enzymes.

In another exemplary embodiment of the present disclosure, the pore may have a size of 0.1-2 nm.

Advantageous Effects

A method for manufacturing enzyme nanoparticles via silica encapsulation of the present disclosure does not include a surface functionalization step and a radical polymerization step. Since a reaction condition is mild, the method is suitable for a large scale production. The silica encapsulated single-enzyme nanoparticles prepared by the method do not include any functionalization or polymerization on the enzyme surface for the formation of silica network and could be surrounded by a thin and porous silica network. The silica network will have a Si—O—Si structure through silica condensation. Some terminal groups which do not form the network may have a structure of Si—OH or Si—O—R (R=alkyl group) to serve as pores. This structure keeps the stability for a long term. Further, differently from the existing silica-capsulated enzyme particles by sol-gel process, the silica encapsulated single-enzyme nanoparticles of the present disclosure have an almost identical $K_m$ value to that of free enzymes, which is not encapsulated with silica and, thus, the maximum reaction rate can be easily reached during the catalytic reaction between the enzymes and substrates.

On the other hand, the reverse micelle synthesis has some problems in that silica condensation like sol-gel process occurs immoderately on the entire enzyme surface because of much water molecules inside reverse micelles. So, the silica network becomes thicker, the pores disappears, and the Michaelis-Menten constant ($K_m$) increases significantly.

The silica network on the enzyme surface can form a chemical bonding with other silica without using crosslinking agents. It means that the —OH groups of silica on the enzyme surface can form chemical bonds through condensation with the —OH groups of silica-based nanostructured materials such as a mesoporous silica at weak acid, neutral pH or weak base. Through this, the silica encapsulated single-enzyme nanoparticles can be immobilized onto the nanostructured materials, thereby improving their stability and varying their applications.

Accordingly, the silica-capsulated single enzyme nanoparticles of the present disclosure can be used in biosensors, biofuel cells, bioremediation, antifouling, quantitative analysis (ELISA), etc. to improve stability and enable more practical industrial application as compared to the existing single enzyme nanoparticles.

BEST MODE

Hereinafter, the embodiments of the present disclosure will be described in detail with reference to accompanying drawings.

As described above, the existing method of encapsulating enzymes in silica sol-gel matrix increase remarkably the Michaelis-Menten constant ($K_m$), which can be translated into resistance to mass transfer because silica matrix encapsulates the aggregate of enzymes, not single enzymes. The existing method for manufacturing single enzyme nanoparticles (SENs) presented to overcome this problem is impossible for a large scale production since it requires the complicated processes of surface functionalization and radical polymerization and is sensitive to reaction conditions.

In order to solve these problems, the present disclosure provides a method for manufacturing silica encapsulated single-enzyme nanoparticles, including: (1) solubilizing enzymes from an aqueous solution into an organic solvent; (2) hydrolyzing the silica by adding silica into the organic solvent and reacting the silica with water molecules on the surface of the solubilized enzymes; (3) back-extracting the enzymes from the organic solvent into an aqueous solution; and (4) condensing the silica in an aqueous solution. The method for manufacturing silica encapsulated single-enzyme nanoparticles according to the present disclosure does not include a surface functionalization step and a radical polymerization. Thus, the method is appropriate for a large scale production during the synthesis of single enzyme nanoparticles. The related procedure is descried referring to FIG. 1.

First, step (1) is to solubilize enzymes in an aqueous solution with an organic solvent. Since silica precursors are dissolved well and stable in organic solvents, silica encapsulation may be performed in an organic solvent.

The aqueous solution used in the present disclosure may be any one capable of maintaining pH suitable for the enzymes, such as a Bis-Tris propane aqueous solution, a sodium phosphate aqueous solution, a Tris aqueous solution, a sodium bicarbonate aqueous solution, etc. Those skilled in the art may easily select the kind and the concentration of the aqueous solution depending on the particular enzymes used.

The organic solvent used in the present disclosure may be any one capable of solubilizing the enzymes and performing silica hydrolysis and condensation. Preferably, a hydrophobic organic solvent such as hexane, heptane, octane, isooctane, etc. may be used alone or in combination.

The solubilization of the enzymes in the aqueous solution with the organic solvent may be performed using an amphiphilic polyethylene glycol or a synthetic polymer based on polyethylene glycol ($PEG_2$). But, specifically, the solubilization may be performed by adding a surfactant to the organic solvent. Although dioctyl sodium sulfosuccinate (AOT), which is an anionic surfactant, was used in the examples of the present disclosure, the surfactant is not limited to AOT and either a cationic or a non-ionic surfactant may be used depending on the enzymes used and their isoelectric point.

In an exemplary embodiment of the present disclosure, the surfactant may be used at or below the critical micelle concentration in order not to form reverse micelles. This allows a small amount of surfactant molecules to solubilize enzymes into organic solvent by forming ion pairs without forming reverse micelles. If reverse micelles are formed, much water molecules are contained inside the reverse micelles, thus resulting in thickening the silica network as well as increasing the Michaelis-Menten constant ($K_m$).

After solubilizing the enzymes in the organic solvent by adding the solubilizing agent such as the surfactant to the organic solvent under shaking, only the organic solvent layer in which the enzymes are solubilized may be separated through centrifugation and so on. If necessary, the organic solvent may be evaporated using nitrogen gas for control of concentration.

The enzymes in the aqueous solution may be dissolved in a suitable buffer and its pH may be controlled variously depending on the isoelectric point of the enzymes. In order to facilitate the solubilization, one or more salt selected from a group consisting of calcium chloride, potassium chloride, sodium chloride and magnesium chloride and one or more alcohol selected from a group consisting of methanol, ethanol, propanol, butanol, pentanol, hexanol and heptanol may be added in small amounts. The salt may be added basically to the aqueous solution and the alcohol may be selected adequately depending on the surfactant and the organic solvent used. A hydrophilic alcohol may be added to an aqueous solution and a hydrophobic alcohol may be added to an organic solvent.

Next, step (2) it to primarily hydrolyze the silica by adding the silica to the organic solvent and reacting it with a small amount of water molecules on the surface of the solubilized enzymes. The silica may be any one that can be dissolved in the organic solvent without limitation. Preferably, the silica may be a silica precursor or a silica powder. Preferably, the silica may be a methoxysilane such as tetramethoxysilane, trimethoxysilane, dimethoxysilane, etc. or an ethoxysilane such as tetraethoxysilane, triethoxysilane, diethoxysilane, etc.

The silica is not particularly limited as long as it can form a silica network on the surface of the enzymes. The silica may be added in an amount of 0.1-10 vol % based on the entire organic solvent, but may not be limited thereto.

After the silica is added to the organic solvent, if the resulting solution is stored at a low temperature of 1-40° C. for 1-5 days, the added silica precursor reacts with a few water molecules on the surface of the solubilized enzymes. As a result, the terminal alkyl group of the silica precursor is converted to an —OH group (hydrolysis) and the formation of silica network is initiated on the surface of the enzymes.

Next, step (3) is to back-extract the enzymes in which the silica network is formed on the surface from the organic solvent into an aqueous solution. Since the amount of water molecules is too small in the organic solvent, the formation of silica network is not enough to improve the stability of the enzymes. Accordingly, it is necessary to extract the enzymes into the aqueous solution to allow condensation by the unreacted silica precursor which is extracted together. For this, the back extraction of the enzymes into the aqueous solution may be performed by stirring for a predetermined time using a back extraction solution.

The back extraction solution is not particularly limited as long as it can extract the enzymes into the aqueous solution. Preferably, a Bis-Tris propane aqueous solution, a sodium phosphate aqueous solution, a Tris aqueous solution, a sodium bicarbonate aqueous solution, etc. may be added to the organic solvent either alone or in combination.

After stirring for the back-extraction, the enzymes and the unreacted silica precursor are extracted into the aqueous solution by the hydrophilic functional groups of the silica network formed on the surface of the enzymes. Then, only the aqueous solution layer may be recovered by centrifugation that separates it from an organic layer. Thereafter, impurities may be filtered out.

Step (4) is to condensing the silica in an aqueous solution. Specifically, the condensation may be performed by storing the enzymes extracted into the aqueous solution at a low temperature (1-40° C.) for a predetermined time (1-5 days). As a result, the unreacted silica is condensed on the surface of the enzymes by lots of water molecules. Thereafter, the unreacted silica particles and the surfactant, etc. may be removed to finally obtain silica encapsulated single-enzyme nanoparticles.

The method for manufacturing silica encapsulated single-enzyme nanoparticles according to the present disclosure does not include a surface functionalization step and a radical polymerization. Thus, the method is appropriate for a large scale production during the synthesis of silica encapsulated single-enzyme nanoparticles.

In an exemplary embodiment of the present disclosure, the silica encapsulated single-enzyme nanoparticles prepared according to the present disclosure include single enzyme nanoparticles and a silica network surrounding the single enzymes and having pores, wherein no covalent bond is formed between the enzyme surface and the silica network.

The single enzyme nanoparticles used in the present disclosure are not particularly limited as long as they can be encapsulated with silica. Preferably, the enzyme may be trypsin, chymotrypsin, pepsin, lipase, glucose oxidase, horseradish peroxidase, tyrosinase, carbonic anhydrase, formaldehyde dehydrogenase, formate dehydrogenase, alcohol dehydrogenase or cholesterol dehydrogenase, but is not limited thereto.

The silica encapsulated single-enzyme nanoparticles prepared according to the present disclosure may have a silica network formed on the surface of the enzymes. The silica network may have a thickness of about 0.5-5 nm, specifically 0.5-2.5 nm, more specifically 0.5-2.0 nm. The thin silica network may comprise no functional group and/or polymer on the surface of the enzymes. Through this, the single enzyme molecules can be encapsulated without forming covalent bonds between the enzyme surface and the silica network.

Further, the silica network will form a Si—O—Si structure through hydrolysis and condensation of the silica. Some terminal groups which does not form the network may have a structure of Si—OH or Si—O—R (R=alkyl group) and these portions can serve as pores. As a result, stability can be maintained even after a long time, and, with comparing to the existing silica-encapsulated enzyme particles via sol-gel process, the silica encapsulated single-enzyme nanoparticles of the present disclosure have an almost identical $K_m$ value to that of free enzymes, which are not encapsulated with silica. Thus, the maximum reaction rate can be easily reached during the catalytic reaction between the enzymes and the substrates.

Consequently, whereas the conventional silica-encapsulated enzyme particles produced via sol-gel process have a higher $K_m$ value as compared to that of free enzymes, the silica encapsulated single-enzyme nanoparticles of the present disclosure may have a $K_m$ value with a margin of error not greater than 20%, more specifically not greater than 10%, more specifically not greater than 5%, most specifically not greater than 3%, as compared to that of free enzymes. As used herein, the free enzymes refer to unencapsulated single enzyme nanoparticles. For example, suppose that the $K_m$ (μM) value of free lipase is 30, the $K_m$ (μM) value of the silica encapsulated single-enzyme nanoparticles of the present disclosure may be specifically 30±6, more specifically 30±0.9. Since the silica encapsulated single-enzyme nanoparticles have a $K_m$ value very similar to that of free enzymes, the silica network on the surface does not induce the mass transfer limitation between the enzymes and the substrates. Therefore, the maximum reaction rate can be quickly reached even when the amount of the substrates is small. Also; the activity of the enzymes can be maintained for a long time.

Whereas the existing enzyme encapsulation method requires the formation of covalent bonds between the enzymes and the silica network by means of adequate functional groups and/or polymers in order to encapsulate multiple enzymes, not single enzyme nanoparticles, at once with silica, the method according to the present disclosure can encapsulate single enzyme nanoparticles without covalent bond between the silica network and the enzyme surface. Accordingly, the present process is simplified and adequate for a large scale production.

In addition, the silica network formed on the enzyme surface according to the present disclosure is advantageous in that it is capable of forming chemical bonding with other silica materials without using a crosslinking agent. This means that the –OH groups of silica on the surface of the enzymes can form chemical bonds through condensation with the —OH groups of silica-based nanostructured materials such as mesoporous silica at weak acid, neutral pH or weak basic. Through this, the silica encapsulated single-enzyme nanoparticles can be immobilized on/in the nanostructured materials. As a result, their stability is further improved and their applications can become more various.

MODE FOR INVENTION

Hereinafter, the present disclosure will be described in detail through examples. However, the following examples are for illustrative purposes only and it will be apparent to those of ordinary skill in the art that the scope of the present disclosure is not limited by the examples.

Example 1

Preparation of Silica Encapsulated Single-Enzyme Nanoparticles

Figure 1:
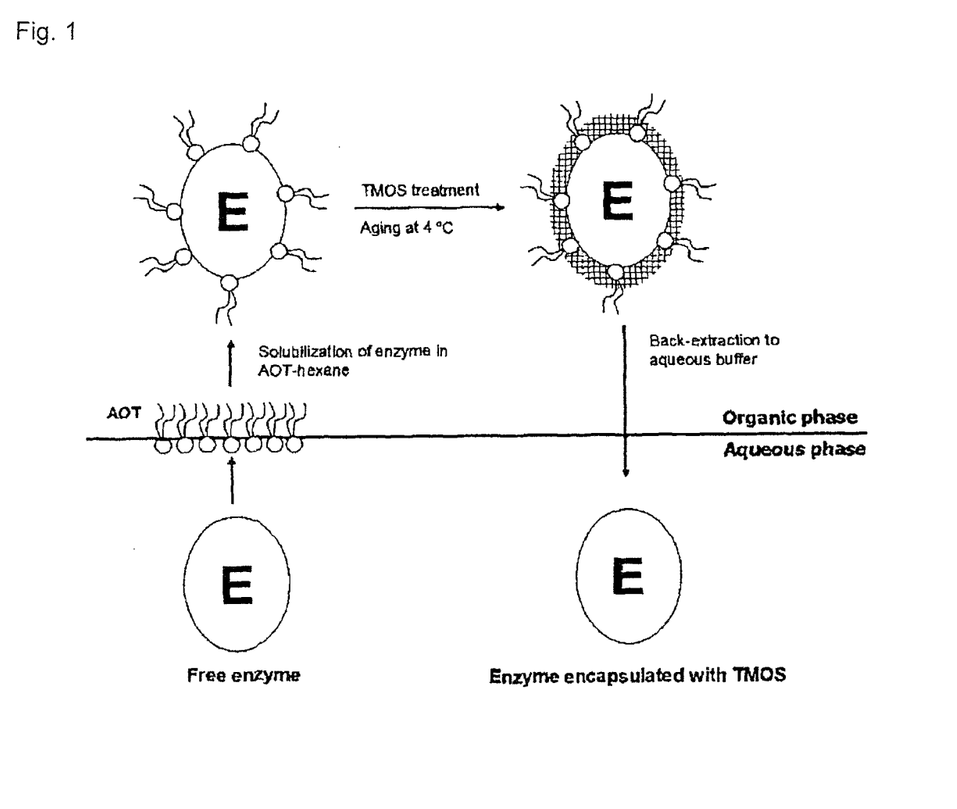
FIG. 1 schematically shows a procedure of manufacturing silica encapsulated single-enzyme nanoparticles (SEENs) according to an exemplary embodiment of the present disclosure.

Silica encapsulated single-enzyme nanoparticles were prepared using α-chymotrypsin (CT) as schematically described in FIG. 1. Specifically, the synthesis of the silica encapsulated single-enzyme nanoparticles began with dissolution of the enzyme in an aqueous solution with an organic solvent. CT was dissolved in a 10 mM Bis-Tris propane (pH 7.8) buffer containing 1% isopropanol and 2 mM calcium chloride to a concentration of 1 mg/mL. Subsequently, 2 mM AOT added to hexane of the same volume was mixed with the enzyme solution. After stirring at room temperature for 15 minutes, phase separation was conducted through centrifugation. Only the hexane layer containing the solubilized enzyme was separated and then hexane was evaporated using nitrogen gas to adjust the concentration to 1 mg/mL.

Next, a mixture solution of TMOS:hexane (1:1) was added to the enzyme-containing hexane solution with a volume of 1% thereof and stored at 4° C. for 17 hours.

Then, after storing for 1.5 hours at room temperature and adding a 200 mM sodium phosphate buffer (pH 7.8) corresponding to 2 times the volume of the hexane, the mixture was stirred at 250 rpm for 10 minutes. After phase separation occurred through centrifugation, only the aqueous solution layer was separated. Then, impurities were filtered off through a 100-nm filter.

Subsequently, the enzyme extracted into the aqueous solution phase was stored at 4° C. for 3 days. After the 3 days, unreacted TMOS and AOT molecules were removed while replacing with a 10 mM sodium phosphate buffer using an ultrafiltration device. The as-synthesized silica encapsulated single-enzyme nanoparticles were stored at 4° C. until use.

Comparative Example 1

Preparation of Reverse Micelle-Silica Encapsulated Single-Enzyme Nanoparticles Using a Reverse Micelle Method Hexane containing 100 mM AOT as surfactant, and a small amount of a 10 mM Bis-Tris propane buffer containing enzymes were added. The amount of the added aqueous solution was adjusted such that its molar concentration was 20 times that of AOT. Then, the enzymes were solubilized to hexane by stirring for 10 minutes. The procedure following the solubilization of the enzymes in hexane was similar to Example 1.

In the reverse micelle method, which was employed for comparison with the method for manufacturing silica encapsulated single-enzyme nanoparticles according to the present disclosure, condensation of the silica precursor proceeds faster because more water molecules are present around the enzyme. As a result, a thicker silica network will be formed and the Michaelis-Menten constant may increase.

Example 2

Confirmation of Silica Network through Measurement of Kinetic Constants and Effect on Mass Transfer of the Substrate The kinetic constants of SEEN-CT (Example 1), RM-SEEN-CT (Comparative Example 1) and free enzyme (free CT) were measured by hydrolysis of MUTMAC. The kinetic constants are given in Table 1. The values were obtained by nonlinear regression based on the least square method.

TABLE 1

|  | kcat (s$^{-1}$) | Km (uM) | kcat/Km (× 10$^5$M$^{-1}$s$^{-1}$) |
|---|---|---|---|
| Free-CT | 31.8 ± 0.8 | 41.8 ± 0.1 | 7.6 ± 0.2 |
| SFFN-CT | 25.4 ± 0.1 | 42.4 ± 0.1 | 6.0 ± 0.1 |
| RM-SEEN-CT | 30.3 ± 0.8 | 76.8 ± 3.6 | 3.9 ± 0.1 |

As seen from Table 1, the $K_m$ value of SEEN-CT was very similar to that of free CT. In contrast, RM-SEEN-CT showed an increased $K_m$ value. Usually, the silica network around the enzymes would act as a barrier, which causes serious mass transfer limitation between the enzyme active sites and substrates with increased Michaelis-Menten constant. However, the $K_m$ value of SEEN-CT (Example 1) was similar to that of free CT (free enzyme) which means that the silica network does not inhibit the substrate transfer from medium to the active sites of enzymes. In contrast, RM-SEEN-CT (Comparative Example 1), which contains a lot of water molecules, had a thicker silica network because of more condensation and showed an increased $K_m$ value. The catalytic efficiency, $k_{cat}/K_m$, of SEEN-CT decreased 21% as compared to free CT and RM-SEEN-CT showed about 48% decrease. The decreased $k_{cat}$ value means that the flexibility of the enzymes decreases because of the silica network formed on the surface of enzymes.

Example 3

Figure 2:
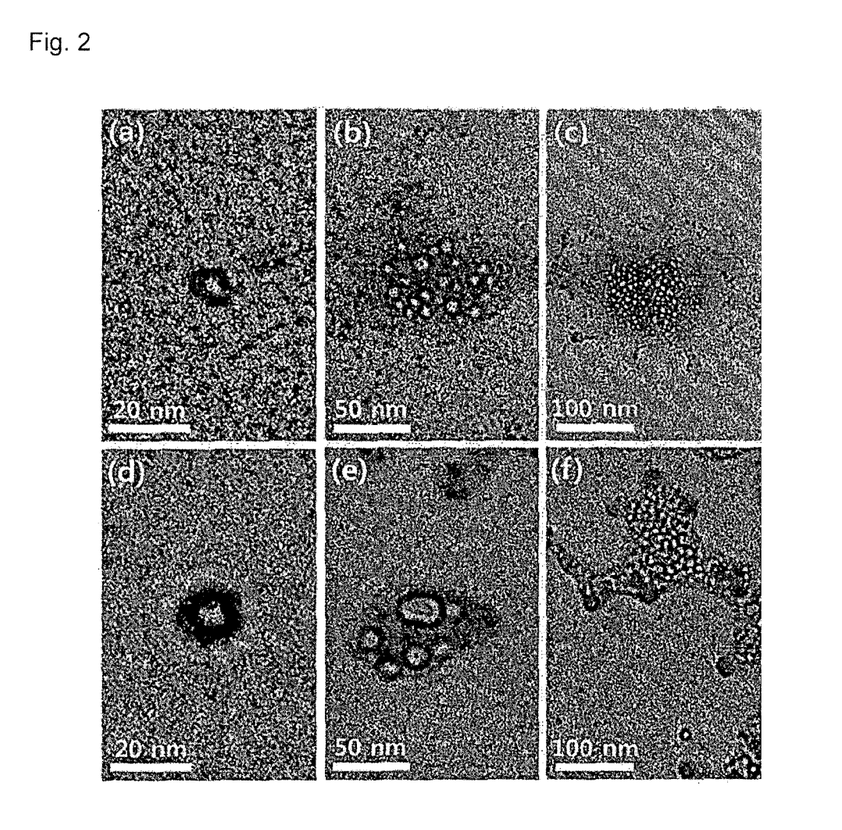
FIG. 2 (a) is a TEM image of SEEN-CT (Example 1) and (b) is a TEM image of RM-SEEN-CT (Comparative Example 1).

Confirmation of Formation of Silica Encapsulated Single-Enzyme Nanoparticles by TEM Imaging and Particle Size thereof by Tapping-Mode AFM FIG. 2 confirms the formation of silica encapsulated single-enzyme nanoparticles by TEM imaging and particle size thereof by tapping mode AFM. Referring to Table 2, the average diameter of free CT, SEEN-CT and RM-SEEN-CT was estimated as 3.9 nm, 6.9 nm and 9.0 nm, respectively. The average thickness of the silica network of SEEN-CT was calculated as 1.5 nm. This means that no aggregation occurred during silica hydrolysis and condensation

TABLE 2

| Sample | Average height | Coating thickness |
|---|---|---|
| Free CT | 3.9 ± 0.8 nm | * |
| SEEN-CT | 6.9 ± 0.5 nm | 1.5 nm |
| RM-SEEN-CT | 9.0 ± 0.7 | 2.5 nm |

Example 4

Confirmation of Improvement of Enzyme Stability by Silica Network

Figure 3:
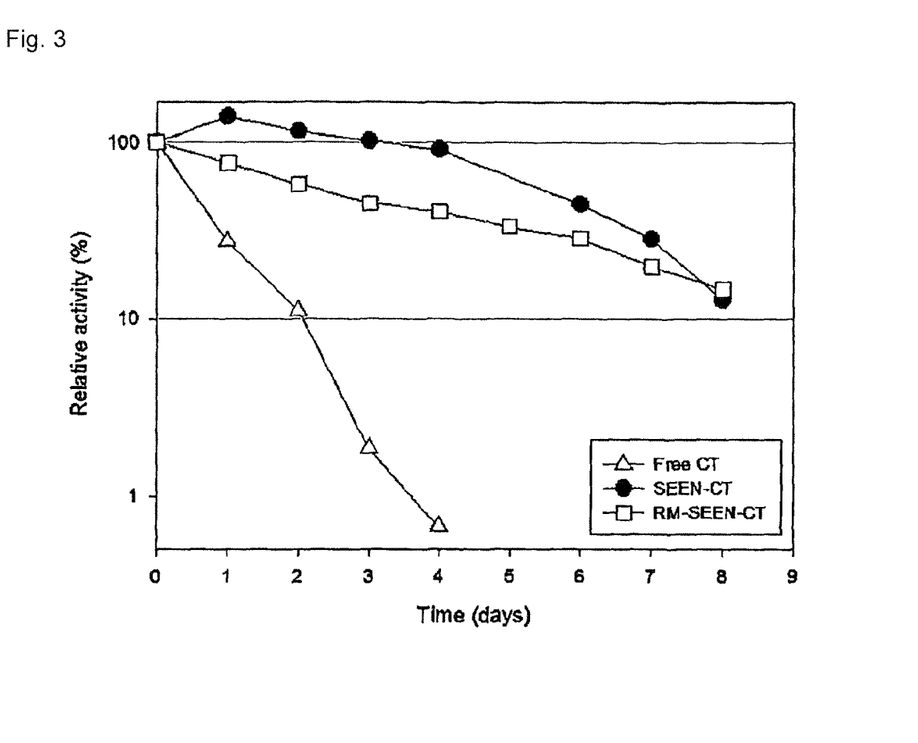
FIG. 3 shows the stability of SEEN-CT (Example 1), RM-SEEN-CT (Comparative Example 1) and free CT (free enzyme) with time under shaking at 200 rpm.

The activity of SEEN-CT, RM-SEEN-CT and free CT was measured by hydrolysis of N-succinyl-Ala-Ala-Pro-Phe p-nitroanilide. FIG. 3 shows the stability of SEEN-CT, RM-SEEN-CT and free CT. Solutions containing SEEN-CT, RM-SEEN-CT and free CT were stored at room temperature under shaking (200 rpm). SEEN-CT (Example 1) retained 90% or more of initial activity after 4 days under the shaking condition, whereas RM-SEEN-CT (Comparative Example 1) showed 47% of initial activity and free CT (free enzyme) showed 7% of initial activity after 4 days. This result means that the silica encapsulation prevents denaturation of the enzymes from the shear stress. The activity of RM-SEEN-CT was decreased because of aggregation caused by serious condensation of the thick silica network.

Example 5

Immobilization of Silica Encapsulated Single-Enzyme Nanoparticles in Mesoporous Silica Immobilization of enzymes on a support through physical or chemical bonding has been widely employed to improve the stability of the enzymes. Many support materials have been used to immobilize enzymes. Particularly, porous materials are advantageous in that a large amount of enzymes can be supported owing to large surface area in pores.

Figure 4:
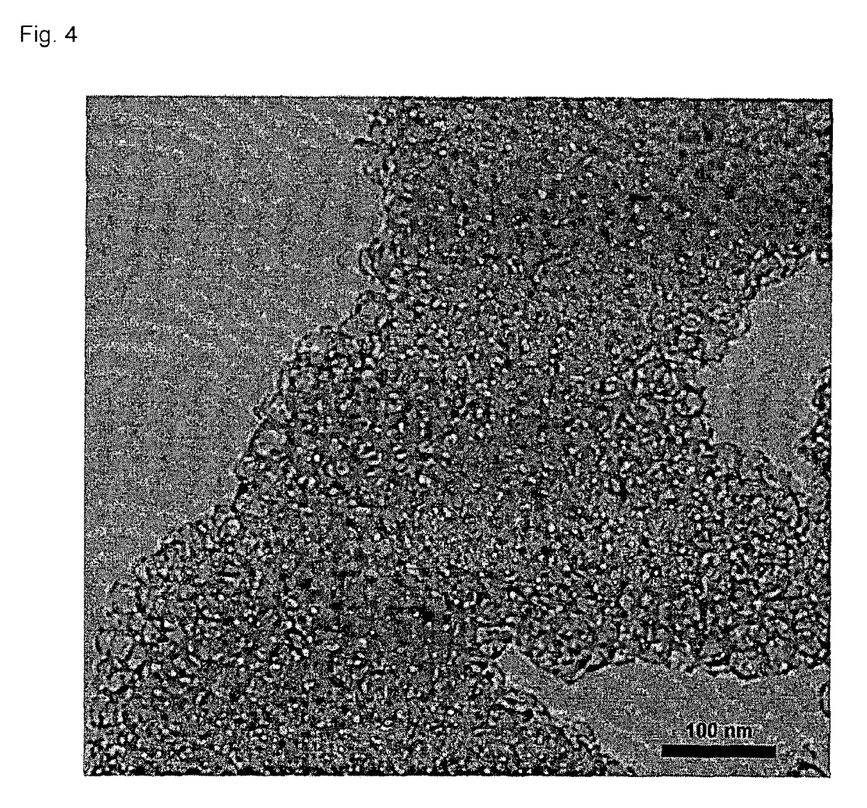
FIG. 4 is a TEM image of MSU-F.

FIG. 4 shows MSU-F which is a mesoporous silica material having an average pore size of 25 nm. It was synthesized using the previously known method. The silica encapsulated single-enzyme nanoparticles were immobilized in MSU-F through condensation of silica to improve stability. The immobilization of the silica encapsulated single-enzyme nanoparticles via hydrolysis and condensation is not limited to MSU-F and any silica-based mesoporous material such as MCM-41, MCM-48, FSM-16, SBA-1, SBA-15, SBA-16, MCF, HMS, MSU-X, IBN-X and PMOs may be used. The mesoporous material has silica residues inside thereof and these residues can form chemical bonding with the silica network of SEEN-CT. In contrast, free CT can be immobilized only by simple physical adsorption.

Figure 5:
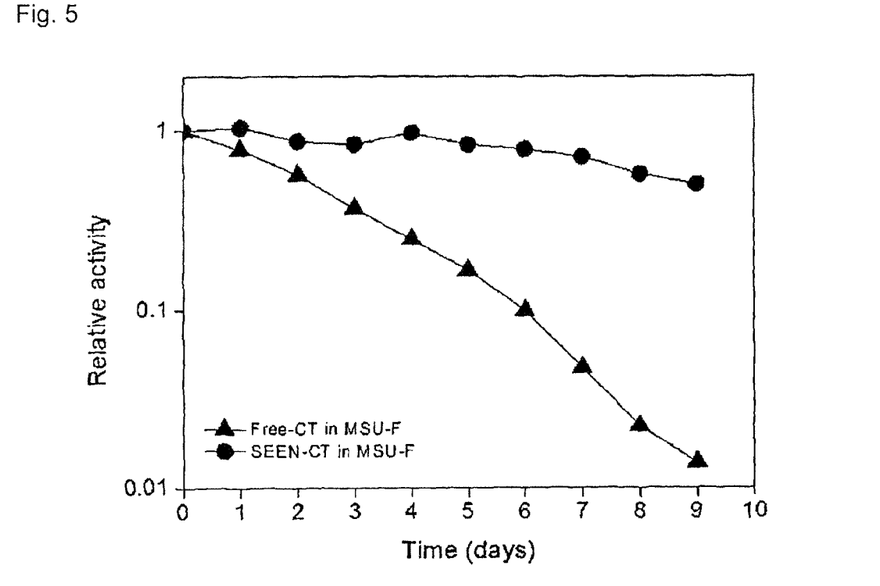
FIG. 5 shows the stability of free CT and SEEN-CT immobilized on MSU-F with time under shaking at 200 rpm.

The immobilization in MSU-F is achieved as follows. The silica encapsulated single-enzyme nanoparticles are mixed with MSU-F and shaken under 200 rpm for 30 minutes. Then, the silica encapsulated single-enzyme nanoparticles adsorbed in MSU-F. After adsorption, washing by 10 mM sodium phosphate buffer was carried out 3 times. Enzyme adsorbed MSU-F was stored at 4° C. for 3 days, then chemical bonding is formed between the silica surface of MSU-F and the silica network of SEEN-CT through condensation. After aging for 3 days, washing by 10 mM sodium phosphate buffer was carried out 3 times, finally. In the resulting structure, the silica encapsulated single-enzyme nanoparticles are protected by the MSU-F and their stability is improved. In terms of stability, SEEN-CT exhibited 92% of initial activity after 5 days under shaking. In contrast, free CT adsorbed in MSU-F retained 20% of initial activity after 5 days under shaking.

Example 6

Silica Encapsulation of Lipase

Figure 6:
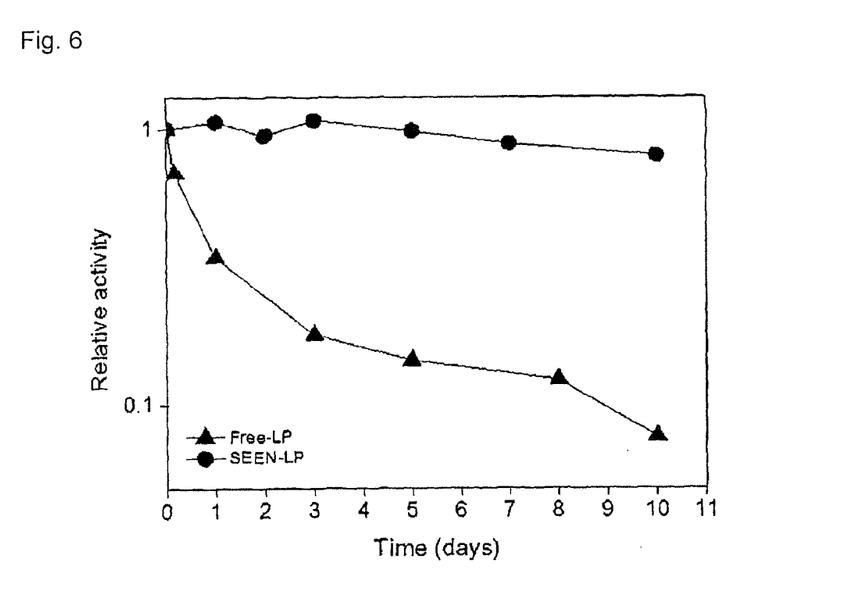
FIG. 6 shows the stability of SEEN-LP with time under shaking at 200 rpm.

The applicability of the silica encapsulation approach of the present disclosure to enzymes other than chymotrypsin (CT) was tested for lipase (LP). The procedure was the same as that for CT described above, except that the buffer pH was changed to 6.5 and the salt was changed to 50 mM sodium chloride. FIG. 6 shows the stability of SEEN-LP and free LP at room temperature under shaking. SEEN-LP and free LP retained 98% and 12% of initial activity, respectively, after 5 days. SEEN-CT exhibited gradually decreased activity because of autolysis of chymotrypsin. In contrast, since lipase does not autolyze, it shows better stability. From the study of the stability of lipase, it was confirmed that the silica encapsulated single-enzyme nanoparticles are applicable to various enzymes.

INDUSTRIAL APPLICABILITY

A method for manufacturing single enzyme nanoparticles through encapsulation with silica, and silica encapsulated single-enzyme nanoparticles manufactured by the same can be applied on biosensors, biofuel cells, bioremediation, antifouling, enzyme-linked immunosorbent assay (ELISA), and so on to improve stability and a large scale production for more practical and industrial applications as compared to the existing single enzyme nanoparticles.

The invention claimed is:

1. Silica encapsulated single-enzyme nanoparticles comprising a single enzyme and a silica network surrounding the single enzyme and having pores, wherein no covalent bond is formed between the single enzyme and the silica network, and the silica encapsulated single-enzyme nanoparticles have a Michaelis-Menten constant ($K_m$) value with a margin of error not greater than 20% as compared to that of free enzymes, and wherein the silica network has a thickness of 0.5-2.0 nm.

2. The silica encapsulated single-enzyme nanoparticles according to claim 1, wherein the silica encapsulated single-enzyme nanoparticles have a Michaelis-Menten constant ($K_m$) value with a margin of error not greater than 10% as compared to that of free enzymes.

3. The silica encapsulated single-enzyme nanoparticles according to claim 1, wherein the silica encapsulated single-enzyme nanoparticles have a Michaelis-Menten constant ($K_m$) value with a margin of error not greater than 3% as compared to that of free enzymes.

4. The silica encapsulated single-enzyme nanoparticles according to claim 1, wherein the pore has a size of 0.1-2 nm.

* * * * *